(12) United States Patent
Gindelberger

(10) Patent No.: US 11,352,337 B1
(45) Date of Patent: Jun. 7, 2022

(54) ZEOLITE CATALYST AND METHOD FOR PREPARATION OF AROMATIC TRICYCLIC PYRANS

(71) Applicant: Acid Neutral Alkaline Laboratory, Longview, WA (US)

(72) Inventor: David Gindelberger, Ladue, MO (US)

(73) Assignee: Acid Neutral Alkaline Laboratory, Longview, WA (US)

( * ) Notice: Subject to any disclaimer, the term of this patent is extended or adjusted under 35 U.S.C. 154(b) by 0 days.

(21) Appl. No.: 17/354,797

(22) Filed: Jun. 22, 2021

Related U.S. Application Data

(60) Provisional application No. 63/195,826, filed on Jun. 2, 2021.

(51) Int. Cl.
| | |
|---|---|
| *C07D 311/80* | (2006.01) |
| *B01J 29/18* | (2006.01) |
| *B01J 37/04* | (2006.01) |
| *B01J 29/65* | (2006.01) |
| *B01J 29/08* | (2006.01) |
| *B01J 29/70* | (2006.01) |
| *C07D 311/78* | (2006.01) |
| *A61K 36/185* | (2006.01) |

(52) U.S. Cl.
CPC .......... *C07D 311/80* (2013.01); *B01J 29/084* (2013.01); *B01J 29/18* (2013.01); *B01J 29/65* (2013.01); *B01J 29/7007* (2013.01); *B01J 37/04* (2013.01); *A61K 36/185* (2013.01); *B01J 2229/38* (2013.01); *B01J 2531/842* (2013.01); *C07D 311/78* (2013.01)

(58) Field of Classification Search
CPC .. B01J 2229/38; B01J 2351/842; B01J 37/04; B01J 2531/842; A61K 36/185; C07D 311/78; C07D 311/80

USPC .......................... 549/388; 424/725, 774, 778
See application file for complete search history.

(56) References Cited

U.S. PATENT DOCUMENTS

| | | | | |
|---|---|---|---|---|
| 5,227,537 A | * | 7/1993 | Stoss ........................ | C07C 37/14 568/619 |
| 7,524,881 B2 | * | 4/2009 | Goodwin ................. | A61P 25/22 514/454 |
| 8,222,292 B2 | * | 7/2012 | Goskonda .................. | A61P 1/08 514/454 |
| 9,345,771 B2 | * | 5/2016 | Goskonda ............ | A61K 9/0095 |
| 9,630,941 B2 | * | 4/2017 | Elsohly ................ | A61K 9/0051 |
| 2004/0143126 A1 | * | 7/2004 | Webster ............... | C07D 311/80 549/390 |
| 2010/0210860 A1 | * | 8/2010 | Erler .................... | C07D 311/80 549/390 |
| 2014/0248379 A1 | * | 9/2014 | Mueller ............... | C07D 311/80 424/725 |
| 2017/0008868 A1 | * | 1/2017 | Dialer .................. | C07D 205/04 |
| 2020/0255389 A1 | * | 8/2020 | Tegen .................. | C07D 311/86 |
| 2021/0198224 A1 | * | 7/2021 | Berkowitz .............. | C07C 37/50 |

* cited by examiner

*Primary Examiner* — Elizabeth D Wood
(74) *Attorney, Agent, or Firm* — Husch Blackwell LLP

(57) ABSTRACT

Provided herein are methods for converting CBD to a product mixture comprising $\Delta^8$-THC, $\Delta^9$-THC, or a combination thereof. The methods provided herein may comprise one or more of (1) a contacting step wherein a starting material comprising CBD, a catalyst comprising a zeolite, and optionally a solvent are added to a reaction vessel, thereby forming a reaction mixture; (2) a conversion step wherein at least a portion of the CBD is converted to THC, thereby forming a product mixture; and (3) optionally, a separation step wherein at least a portion of the catalyst is removed from the product mixture. Advantageously, the methods do not require the use of catalysts or other reagents that are hazardous to human health.

24 Claims, No Drawings

ZEOLITE CATALYST AND METHOD FOR PREPARATION OF AROMATIC TRICYCLIC PYRANS

BACKGROUND

In recent years, there has been increasing interest in the medicinal properties of cannabinoids, which are a family of chemical compounds derived from the *cannabis* plant. For example, cannabidiol (CBD) has long been used as an antiepileptic medication, and the potential use of CBD to treat other neurological disorders is an area of active research. Likewise, while tetrahydrocannabinol (THC) is known as the principal psychoactive constituent of *cannabis*, recent research has identified potential uses of THC to treat a variety of diseases, including chronic pain, spasticity, and symptoms associated with multiple sclerosis and other neurological disorders.

More recently, research has indicated that different isomers of THC may provide different beneficial effects. For example, $\Delta^8$-THC is a double-bond isomer of $\Delta^9$-THC.

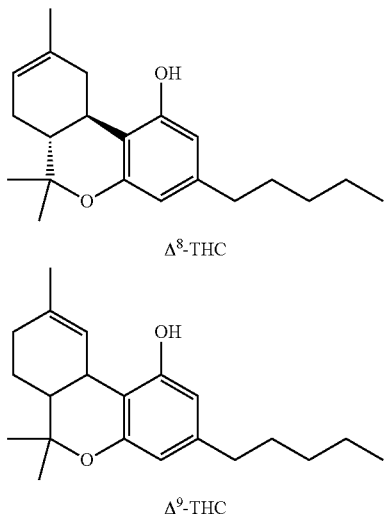

While both isomers are psychoactive, it is currently believed that $\Delta^8$-THC is less potent in this regard than $\Delta^9$-THC. Conversely, $\Delta^8$-THC is believed to be a more potent antiemetic agent than $\Delta^9$-THC.

Industrial hemp comprises CBD in an amount of about 2% by weight, which is significantly greater than either $\Delta^8$-THC (approximately 0.2% by weight) or $\Delta^9$-THC (approximately 0.1% by weight). Methods of converting CBD to $\Delta^8$-THC and $\Delta^9$-THC are therefore desirable. To date, however, a limited amount of research has been performed to identify such methods. For example, U.S. Pat. No. 7,399,872 to Webster et al. utilized a Lewis acid catalyst to promote the conversion of CBD to $\Delta^8$-THC and $\Delta^9$-THC. Unfortunately, the catalysts disclosed by Webster et al. (p-toluenesulfonic acid, boron trifluoride, and $BF_3Et_2O$) are all extremely hazardous to human health. This presents a safety hazard for persons who handle such materials, and also raises concerns about the presence of residual catalyst in the final products, which are intended for human consumption.

It is therefore desirable to develop new methods of efficiently converting CBD to $\Delta^8$-THC and $\Delta^9$-THC. Preferably, such methods would not require the use of catalysts or other reagents that are hazardous to human health. It is further desirable to develop methods that provide an improved degree of control over the relative proportion of $\Delta^8$-THC to $\Delta^9$-THC generated by the reaction.

SUMMARY

Provided herein are methods of converting CBD to THC. The methods provided herein may comprise one or more of (1) a contacting step wherein a starting material comprising CBD, a catalyst comprising a zeolite, and optionally a solvent are added to a reaction vessel, thereby forming a reaction mixture; (2) a conversion step wherein at least a portion of the CBD is converted to THC, thereby forming a product mixture; and (3) a separation step wherein the catalyst is removed from the product mixture.

For example, provided herein is a method of converting CBD to THC, the method comprising contacting a starting material comprising CBD with a catalyst comprising a zeolite, thereby forming a reaction mixture, and heating the reaction mixture to a temperature of at least about 100° C. for a period of at least about 30 minutes, thereby forming a product mixture comprising THC.

Also provided herein is method of converting CBD to THC, the method comprising (1) a contacting step, wherein a starting material comprising CBD is contacted with a catalyst comprising a zeolite, thereby forming a reaction mixture; and (2) a conversion step, wherein CBD in the reaction mixture is converted to THC, thereby forming a product mixture comprising THC.

Also provided herein is a cannabinoid composition comprising THC, wherein the composition is produced by a method as provided herein.

Other objects and features will be in part apparent and in part pointed out hereinafter.

DETAILED DESCRIPTION

Provided herein are methods for converting CBD to a product mixture comprising THC. Preferably, the product mixture comprises $\Delta^8$-THC, $\Delta^9$-THC, or a combination thereof. The methods utilize a catalyst comprising a zeolite, which is commonly used as a catalyst and sorbant. The zeolite is comprised of aluminosilicates are generally regarded as safe for human consumption and are listed as an approved inactive ingredient by the FDA. Advantageously, the methods described herein do not require the use of catalysts or other reagents that are hazardous to human health.

Definitions

As used herein, CBD refers to cannabidiol.

As used herein, THC refers to tetrahydrocannabinol, and is inclusive of isomers including $\Delta^8$-THC and $\Delta^9$-THC.

As used herein, $\Delta^8$-THC refers to $\Delta^8$-tetrahydrocannabinol.

As used herein, $\Delta^9$-THC refers to $\Delta^9$-tetrahydrocannabinol.

Components

The methods provided herein may utilize one or more of (1) a starting material comprising CBD; (2) a catalyst comprising a zeolite; and (3) optionally, a solvent. These components are described in further detail below.

Starting Material

The methods provided herein may utilize a starting material comprising CBD. The starting material may comprise, for example, *Cannabis* plant material (e.g., industrial hemp) or an extract thereof.

In preferred embodiments, the starting material comprises substantially pure CBD. For example, the starting material preferably comprises CBD in an amount of at least about 50%, at least about 60%, at least about 70%, at least about 80%, at least about 90%, or at least about 95% by weight.

The starting material may comprise, consist essentially of, or consist of a CBD distillate or CBD isolate. A particularly preferred starting material is CBD isolate.

Zeolite Catalyst

The methods provided herein may utilize a catalyst comprising a zeolite.

As understood by those skilled in the art, zeolites are solid state, microporous, aluminosilicate materials. Suitable zeolites may, for example, include compounds having the general molecular formula of

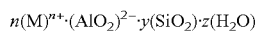

wherein M is a cation with positive charge that is equal to n; y is an average number greater than zero; and z is an average number greater than zero. In preferred embodiments, y is less than or equal to 1.

The catalyst may comprise a natural zeolite, a synthetic zeolite, or a combination thereof. Non-limiting examples of natural zeolites include analcime, chabazite, clinoptilolite, erionite, mordenite, phillipsite, and ferrierite. Non-limiting examples of synthetic zeolites include Linde Type A, Linde Type B (zeolite P), Linde Type F, Linde Type L, Linde Type W, Linde Type X, Linde Type Y, Silicalite-1, ZSM-5, SSZ-32, and Zeolite-Beta.

Without being bound to a particular theory, it is currently believed that the zeolite catalyzes the conversion of CBD to THC by cationic activation of the exocyclic olefin in CBD. Notably, it has been observed that silica gel (silicon oxides) or alumina (aluminum oxide) alone does not catalyze the conversion of CBD to THC.

Solvent

The methods disclosed herein is enable the conversion of CBD to THC without the use of a solvent. In many cases, this represents a significant advantage; if desired, the reaction can be carried out using only two components (e.g., a starting material comprising CBD, and a catalyst comprising a zeolite).

In some cases, however, the use of a solvent may be desirable. For example, a solvent may improve the ease of processing the product mixture, which can be difficult to work with due to the high viscosity of THC. In some cases, the final product is a dosage form that requires the presence of a solvent, and adding the solvent during the process described herein is therefore convenient. In still further cases, and again without being bound to a particular theory, it is believed that the presence of a solvent may affect the relative amounts of minor cannabinoids (i.e., cannabinoids other than CBD or THC) produced during the conversion step. Non-limiting examples of suitable solvents include alcohols, alkanes, edible oils, and any other emulsifiers or surfactants approved for use in pharmaceutical formulations.

The solvent may comprise an alcohol. The alcohol may be, for example, a $C_1$ to $C_6$ organic alcohol. Non-limiting examples of suitable alcohols include methanol, ethanol, and isopropanol. A preferred solvent is isopropanol.

The solvent may comprise an alkane. The alkane may be, for example, a $C_1$ to $C_{10}$ alkane, more preferably a $C_5$ to $C_8$ alkane. Non-limiting examples of preferred alkanes include hexane and heptane.

The solvent may comprise an edible oil. For example, the solvent may comprise a vegetable oil. A preferred solvent is coconut oil. The use of an edible oil is particularly desirable were the desired final product is an edible formulation. In those cases, an edible oil (e.g., coconut oil) may be used as a solvent and simply carried through into the final, edible formulation.

The solvent may comprise one or more emulsifiers or surfactants approved for use in pharmaceutical formulations. Non-limiting examples of suitable emulsifiers and surfactants include ethoxylated fatty acid derivatives (e.g., polyoxyl stearate) and polysorbate-type nonionic surfactants. For example, the solvent may comprise polyoxyl stearate.

Reaction Procedure

The methods provided herein may comprise one or more of (1) a pH adjustment step wherein a catalyst comprising a zeolite is contacted with a base; (2) a contacting step wherein a starting material comprising CBD, a catalyst comprising a zeolite, and optionally a solvent are added to a reaction vessel, thereby forming a reaction mixture; (3) a conversion step wherein at least a portion of the CBD is converted to THC, thereby forming a product mixture; (4) a separation step wherein the catalyst is removed from the product mixture. These steps are described in further detail below.

pH Adjustment Step

The methods provided herein may comprise a pH adjustment step wherein a catalyst comprising a zeolite is contacted with a base.

The base is preferably a weak base. A non-limiting example of a preferred base is sodium bicarbonate.

The pH adjustment step may comprise contacting the zeolite catalyst and the base for a period of at least about 15 minutes, at least about 30 minutes, at least about 1 hour, at least about 1.5 hours, at least about 2 hours, at least about 2.5 hours, at least about 3 hours, at least about 3.5 hours, at least about 4 hours, at least about 4.5 hours, at least about 5 hours, at least about 6 hours, at least about 7 hours, or at least about 8 hours. For example, the conversion step may comprise heating the reaction mixture for a period of from about 15 minutes to about 6 hours, from about 20 minutes to about 3 hours, or from about 30 hours to about 3 hours.

In preferred embodiments, a zeolite catalyst that is treated with a pH adjustment step as described herein will produce an alkalkine solution when dissolved in water. For example, suspending 100 mg of the zeolite catalyst in 5 ml distilled water will preferably yield a mixture having a pH of at least about 7, at least about 7.5, at least about 8, at least about 8.5, or at least about 9. In preferred embodiments, suspending 100 mg of the zeolite catalyst in 5 ml distilled water will preferably yield a mixture having a pH of at from about 7 to about 10, from about 7.5 to about 9.5, from about 8 to about 9.5, or from about 8.5 to about 9.5.

As used herein, the term "alkaline zeolite catalyst" refers to a zeolite catalyst wherein suspending 100 mg of the zeolite catalyst in 5 ml distilled water yields a mixture having a pH of greater than 7.

The pH adjustment step may further comprise drying the zeolite catalyst. The catalyst may be dried, for example, at a temperature of at least about 30° C., at least about 35° C., at least about 40° C., at least about 45° C., or at least about 50° C. The catalyst may be dried for a period of at least about 30 minutes, at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, or at least about 12 hours or more. Optionally, the catalyst may be dried under a vacuum.

Contacting Step

The methods provided herein may comprise a contacting step wherein a starting material comprising CBD, a catalyst comprising a zeolite, and optionally a solvent are added to a reaction vessel, thereby forming a reaction mixture.

The components may be added in any order. Preferably, the starting material is added first, followed by the catalyst, and optionally followed by the solvent.

Optionally the reaction mixture may be stirred (e.g., using a stir bar).

If a solvent is used, the reaction mixture may be heated in order to fully dissolve the CBD in the solvent. The reaction mixture may be heated, for example, to a temperature of at least about 30° C., at least about 40° C., at least about 50° C., or at least about 60° C. in order to dissolve the CBD. Typically, when a solvent is used, the reaction mixture is heated to a temperature of from about 30° C. to about 70° C., from about 40° C. to about 70° C., or from about 45° C. to about 65° C. in order to dissolve the CBD.

Typically, the reaction mixture comprises the starting material in an amount of at least about 80% by weight, for example, at least about 90%, at least about 95%, at least about 96%, at least about 97%, at least about 98%, or even at least about 99% by weight. Correspondingly, the reaction mixture typically comprises CBD in an amount of at least about 80% by weight, for example, at least about 90%, at least about 95%, at least about 96%, at least about 97%, at least about 98%, or even at least about 99% by weight.

The reaction mixture may comprise the zeolite catalyst in an amount of from about 0.1% by weight to about 20% by weight, for example, from about 1% by weight to about 10% by weight, from about 0.5% by weight to about 5% by weight, or from about 1% by weight to about 5% by weight. Typically, the reaction mixture comprises the zeolite catalyst in an amount of less than about 20% by weight, less than about 15% by weight, or less than about 10% by weight.

The reaction mixture may comprise CBD and the zeolite catalyst in a molar ratio of at least about 1:1, for example, at least about 2:1, at least about 2.5:1, at least about 3:1, at least about 3.5:1, at least about 4:1, at least about 5:1, at least about 6:1, at least about 10:1, or at least about 20:1, at least about 50:1, at least about 100:1, at least about 150:1, or even at least about 200:1. For example, the reaction mixture may comprise CBD and the zeolite catalyst in a molar ratio of from about 1:1 to about 80:1, such as from about 2:1 to about 60:1, or from about 3:1 to about 50:1.

Conversion Step

The methods provided herein may further comprise a conversion step wherein at least a portion the CBD starting material is converted to THC, thereby providing a product mixture comprising $\Delta^8$-THC, $\Delta^9$-THC, or a combination thereof.

The conversion step may comprise heating the reaction mixture. For example, the reaction mixture may be heated to a temperature of at least about 70° C., at least about 80° C., at least about 90° C., at least about 100° C., at least about 110° C., at least about 120° C., or at least about 125° C. Typically, the conversion step is carried out at a temperature of from about 80° C. to about 200° C., for example, from about 100° C. to about 185° C., or from about 125° C. to about 175° C.

The conversion step may comprise heating the reaction mixture for a period of at least about 30 minutes, at least about 1 hour, at least about 1.5 hours, at least about 2 hours, at least about 2.5 hours, at least about 3 hours, at least about 3.5 hours, at least about 4 hours, at least about 4.5 hours, or at least about 5 hours. For example, the conversion step may comprise heating the reaction mixture for a period of from about 30 minutes to about 6 hours, from about 1 hour to about 6 hours, from about 2 hours to about 6 hours, from about 2.5 hours to about 6 hours, or from about 2.5 hours to about 5 hours.

Without being bound to a particular theory, it has been observed that at higher temperatures, the reaction proceeds more rapidly The conversion step may be carried out under ambient air. Alternatively, the conversion step may be carried out under an atmosphere comprised substantially of nitrogen. As a further alternative, the conversion step may be carried out under vacuum conditions.

Optionally, the progress of the reaction may be monitored by periodically taking samples of the liquid reaction mixture and analyzing them, for example using gas chromatography (GC) or high pressure liquid chromatography (HPLC). For example, the reaction may be monitored by collecting a sample of the reaction mixture every 30 to 60 minutes.

The conversion step may further comprise cooling the reaction mixture to halt the conversion of CBD to THC. The reaction may be stopped by cooling the reaction mixture to a temperature of less than about 80° C., for example, less than about 70° C., less than about 60° C., less than about 50° C., less than about 45° C., or less than about 40° C.

Product Mixture

The conversion step provides a product mixture that comprises $\Delta^8$-THC, $\Delta^9$-THC, or a mixture thereof. The product mixture may further comprise unreacted CBD, and optionally other cannabinoids (which may be referred to herein as minor cannabinoids).

Typically, at least about 5% by weight, at least about 10% by weight, at least about 15% by weight, at least about 20% by weight, at least about 25% by weight, at least about 30% by weight, at least about 40% by weight, or at least about 45% by weight of the CBD in the starting material is converted to THC. In preferred embodiments of the methods provided herein, at least about 50% by weight of the CBD in the starting material is converted to THC. For example, in preferred embodiments at least about 60% by weight, at least about 70% by weight, at least about 80% by weight, or at least about 90% by weight of the CBD in the starting material is converted to THC.

The product mixture may comprise a mixture of $\Delta^8$-THC and $\Delta^9$-THC. In some embodiments, the ratio of $\Delta^8$-THC to $\Delta^9$-THC in the product mixture is approximately 1:1. For example, the ratio of $\Delta^8$-THC to $\Delta^9$-THC in the product mixture may range from about 20:1 to about 1:20, from about 10:1 to about 1:10, from about 4:1 to about 1:4, from about 3:1 to about 1:3, from about 2:1 to about 1:2, or from about 1.5:1 to about 1:0.75.

In some embodiments, $\Delta^9$-THC comprises a significant percentage of the total amount of THC in the product mixture. For example, $\Delta^9$-THC may comprise at least about 5%, at least about 10%, at least about 20%, at least about 40%, at least about 50%, at least about 60%, at least about 70%, at least about 75%, or at least about 80% of the total amount of THC in the product mixture.

In some embodiments, the product mixture may comprise $\Delta^9$-THC in excess relative to $\Delta^8$-THC. For example, the product mixture may comprise $\Delta^9$-THC in a ratio, relative to $\Delta^8$-THC, of greater than 1:1. The ratio of $\Delta^9$-THC to $\Delta^8$-THC in the product mixture may be at least about 1.5:1, at least about 1.75:1, at least about 2:1, at least about 2.5:1, at least about 3:1, at least about 4:1, at least about 5:1, at least about 10:1, at least about 15:1, or even at least about 20:1.

Separation Step

The methods provided herein may further comprise a separation step wherein at least a portion of the catalyst is removed from the product mixture.

If desired, the zeolite catalyst may be separated from the reaction product using methods known to those skilled in the art. For example, the zeolite catalyst may be removed by filtration.

When a solvent is present, the reaction mixture is preferably cooled prior to filtration. The reaction mixture may be cooled in ambient air, or alternatively by placing a container comprising the reaction mixture into a cool water bath. For example, the reaction mixture may be cooled to a temperature of less than about 70° C., less than about 65° C., or less than about 60° C. prior to filtration. For example, the reaction mixture may be cooled to a temperature of from about 60° C. to about 70° C. prior to filtration.

Alternatively, when no solvents are present, it is preferable to filter the reaction mixture at a relatively warmer temperature. For example, the filtration step may be carried out at a temperature of from about 70° C. to about 80° C.

Cannabinoid Compositions

Also provided herein is a cannabinoid composition comprising THC, wherein the composition is produced by a method as described above.

For example, the cannabinoid composition may comprise a product mixture as described above. The composition may, for example, comprise $\Delta^8$-THC and/or $\Delta^9$-THC in any of the amounts, concentrations, or ratios as described above with respect to the product mixture.

EXAMPLES

The following non-limiting examples are provided to further illustrate the present disclosure.

General Reaction Procedure

The reaction procedure described below was used in each of the following examples, unless otherwise indicated. In general, the reaction converts CBD in the starting material to a mixture of $\Delta^8$-THC and $\Delta^9$-THC.

CBD isolate is placed in a reaction container and a zeolite is added. Optionally, a solvent is added and the mixture warmed to above 60° C. The reaction is then run at a temperature between 80° C. and 200° C. The reaction is monitored by high pressure liquid chromatography (HPLC), and when the target conversion of CBD to THC is achieved, the reaction is stopped by cooling to a temperature of less than about 80° C. by placing a container comprising the reaction mixture into a cool water bath.

The zeolite catalyst is then removed by filtering the reaction mixture with a fritted glass filter or, alternatively with a paper filter in a buchner. When a solvent is present, the reaction mixture is cooled to a temperature of 60° C. prior to filtration. When no solvents are present, the reaction mixture is filtered at a relatively warmer temperature of approximately 80° C., and then cooled further.

Cannabinoids present in the reaction product were identified by HPLC retention time after having established the method with known standards. The ratio of $\Delta^9$-THC to $\Delta^8$-THC in the reaction product was observed to depend on temperature, time and catalyst charge. In some cases, small amounts of other minor cannabinoids were also produced.

In the examples described below, HPLC was carried out using a Waters 2795 equipped with a standard USP-L1 column, and a Waters 2487 UV detector. A methanol/water gradient was used to elute the samples. The detector was set to 228 nm. Samples were dissolved in methanol/water, centrifuged and injected in 5-10 µl volumes. Thermo-Fisher "Xcalibur" version 4.4 software was used to acquire and integrate the UV data. pH measurements were performed with a Apera MP511 pH meter with stock pH probe. The meter was calibrated with standards at pH of 4.0, 7.0 and 10.0.

Example 1

CBD (1.0 g) and Zeolite-B 'H' form (0.15 g) were combined in a vial and warmed to 100° C. with stirring. After 8 hours the cannabinoid content of the product mixture consisted of 23.1% CBD, 24.9% $\Delta^8$-THC, and 48.1% $\Delta^9$-THC, with the remainder being minor cannabinoids.

Example 2

CBD (1.0 g) and Zeolite-Y 'H' form (0.15 g) were combined in a vial and warmed to 100° C. with stirring. After 8 hours the cannabinoid content of the product mixture consisted of 12.1% CBD, 30.8% $\Delta^8$-THC, and 53.7% $\Delta^9$-THC, with the remainder being minor cannabinoids.

Suspending 100 mg of the zeolite in 5 ml distilled water gave a pH reading of 6.1.

Example 3

CBD (1.2 g) and Zeolite-Y 'H' form (0.57 g) were combined in a vial with 2 ml hexanes and warmed in a sealed vial to 100° C. with stirring. After 12 hours the cannabinoid content of the product mixture consisted of 17.9% CBD, 33.2% $\Delta^8$-THC, and 53.2% $\Delta^9$-THC, with the remainder being minor cannabinoids.

Example 4

CBD (1.1 g) and Zeolite-B 'H' form (0.53 g) were combined in a vial with 2 ml hexanes and warmed to 100° C. in a sealed vial with stirring. After 2 hours the cannabinoid content of the product mixture consisted of 2.3% CBD, 36.9% $\Delta^8$-THC, and 54.3% $\Delta^9$-THC, with the remainder being minor cannabinoids.

Example 5

CBD (1.1 g) and Zeolite-Y 'H' form (0.60 g) were combined in a vial with 2 ml isopropanol and warmed to 100° C. in a sealed vial with stirring. After 8 hours the cannabinoid content of the product mixture consisted of 67.1% CBD, 20.4% $\Delta^8$-THC, and 11.5% $\Delta^9$-THC, with the remainder being minor cannabinoids.

Example 6

Prior to reaction, 1.5 g of Zeolite-Y '''' form was suspended in 10 ml distilled water and 3 g of sodium bicarbonate was added. This mixture was stirred 1 hour, filtered and the zeolite washed 3 times with 10 ml distilled water and once with 10 ml ethanol. The zeolite was dried approximately 2 hours in a vacuum oven at 50° C. Suspending 100 mg of the zeolite in 5 ml distilled water gave a pH reading of 9.2. CBD (5.0 g) was combined with the treated catalyst (0.6 g) under vacuum. The mixture was warmed to 175° C. for 2 hours. The cannabinoid content of the product mixture consisted of 4.2% CBD, 13.4% $\Delta^8$-THC, and 73.9% $\Delta^9$-THC, with the remainder being minor cannabinoids.

Example 7

Prior to reaction, 1.0 g of Zeolite-Y "'" form was suspended in 10 ml distilled water and 2.3 g of calcium acetate was added. This mixture was stirred 2 hours, filtered and the zeolite washed 3 times with 10 ml distilled water and once with 10 ml ethanol. The zeolite was dried approximately 2 hours in a vacuum oven at 50° C. CBD (0.9 g) was combined with the treated catalyst (0.1 g). The mixture was warmed to 175° C. for 5 minutes. The cannabinoid content of the product mixture consisted of 68.6% CBD, 7.5% $\Delta^8$-THC, and 22.9% $\Delta^9$-THC, with the remainder being minor cannabinoids.

Example 8

Prior to reaction, 1.0 g of Zeolite-Y "'" form was suspended in 10 ml distilled water and 30 mg of sodium bicarbonate was added. This mixture was stirred 1 hour, filtered and the zeolite washed 3 times with 10 ml distilled water and once with 10 ml ethanol. The zeolite was dried approximately 12 hours in a vacuum oven at 50° C. Suspending 100 mg of the zeolite in 5 ml distilled water gave a pH reading of 8.4. CBD (1.1 g) was combined with the treated catalyst (0.1 g). The mixture was warmed to 150° C. for 1 hour. The cannabinoid content of the product mixture consisted of 52.3% CBD, 11.6% $\Delta^8$-THC, and 32.7% $\Delta^9$-THC, with the remainder being minor cannabinoids.

Example 9

Prior to reaction, 1.0 g of Zeolite-Y "'" form was suspended in 10 ml distilled water and 60 mg of sodium bicarbonate was added. This mixture was stirred 1 hour, filtered and the zeolite washed 3 times with 10 ml distilled water and once with 10 ml ethanol. The zeolite was dried approximately 12 hours in a vacuum oven at 50° C. Suspending 100 mg of the zeolite in 5 ml distilled water gave a pH reading of 8.5. CBD (1.1 g) was combined with the treated catalyst (0.1 g). The mixture was warmed to 150° C. for 1 hour. The cannabinoid content of the product mixture consisted of 72.4% CBD, 5.0% $\Delta^8$-THC, and 19.1% $\Delta^9$-THC, with the remainder being minor cannabinoids.

Example 10

Prior to reaction, 1.0 g of Zeolite-Y "'" form was suspended in 10 ml distilled water and 200 mg of sodium bicarbonate was added. This mixture was stirred 1 hour, filtered and the zeolite washed 3 times with 10 ml distilled water and once with 10 ml ethanol. The zeolite was dried approximately 12 hours in a vacuum oven at 50° C. Suspending 100 mg of the zeolite in 5 ml distilled water gave a pH reading of 9.1. CBD (1.1 g) was combined with the treated catalyst (0.1 g). The mixture was warmed to 150° C. for 1 hour. The cannabinoid content of the product mixture consisted of 80.7% CBD, 3.7% $\Delta^8$-THC, and 13.2% $\Delta^9$-THC, with the remainder being minor cannabinoids.

Example 11

Prior to reaction, 1.0 g of Zeolite-Y "'" form was suspended in 10 ml distilled water and 1 ml of 30% ammonium hydroxide was added. This mixture was stirred 1 hour, filtered and the zeolite washed 3 times with 10 ml distilled water and once with 10 ml ethanol. The zeolite was dried approximately 12 hours in a vacuum oven at 50° C. Suspending 100 mg of the zeolite in 5 ml distilled water gave a pH reading of 9.0. CBD (1.0 g) was combined with the treated catalyst (0.2 g). The mixture was warmed to 175° C. for 3 hours. The cannabinoid content of the product mixture consisted of 55.0% CBD, 8.5% $\Delta^8$-THC, and 25.5% $\Delta^9$-THC, with the remainder being minor cannabinoids.

Example 12

CBD (0.9 g) and Zeolite-ZSM5 "$NH_4^+$" form (0.2 g) were combined in a vial and warmed to 175° C. with stirring. After 1 hour the cannabinoid content of the product mixture consisted of 69.4% $\Delta^8$-THC, and 0.8% $\Delta^9$-THC, with the remainder being a mixture of unidentified cannabinoids eluting close to $\Delta^9$-THC.

Example 13

CBD (1.0 g) and Mordenite "$NH_4^+$" form (0.2 g) were combined in a vial and warmed to 175° C. with stirring. After 8 hours the cannabinoid content of the product mixture consisted of 44.8% CBD, 16.0% $\Delta^8$-THC, and 32.6% $\Delta^9$-THC, with the remainder being minor cannabinoids.

Example 14

CBD (1.0 g) and Ferrierite "$NH_4^+$" form (0.2 g) were combined in a vial and warmed to 175° C. with stirring. After 8 hours the cannabinoid content of the product mixture consisted of 62.2% $\Delta^8$-THC, and 1.7% $\Delta^9$-THC, with the remainder being a mixture of unidentified cannabinoids eluting close to $\Delta^9$-THC.

Example 15

CBD (1.04 g) and previously used buffered Zeolite Y form (0.2 g) were combined in a round bottom and warmed to 175° C. under vacuum with stirring. After 1 hour the cannabinoid content of the product mixture consisted of 72.6% $\Delta^9$-THC, 14.7% $\Delta^8$-THC, and 3.3% CBD with the remainder being minor cannabinoids eluting close to $\Delta^9$-THC.

Example 16

Ferrierite "$NH_4^+$" form (5.2 g) and iron (III) sulfate hydrate (6.0 g) were mixed in 30 ml distilled water for 1 hour. The zeolite suspension was filtered, washed with 3×30 ml distilled water and 30 ml ethanol then dried in a vacuum oven at 80° C. for 45 minutes. CBD (1.6 g) and the iron-treated ferrierite (0.1 g) were combined in a vial and warmed to 150° C. with stirring. After 30 minutes the cannabinoid content of the product mixture consisted of 22.3% Δ9-THC, 13.7% Δ8-THC, and 62.5% CBD with the remainder being minor cannabinoids eluting close to Δ9-THC.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

In view of the above, it will be seen that the several objects of the disclosure are achieved and other advantageous results attained.

As various changes could be made in the above products and methods without departing from the scope of the disclosure, it is intended that all matter contained in the above description shall be interpreted as illustrative and not in a limiting sense.

What is claimed is:

1. A method of converting CBD to THC, the method comprising:
   (1) a contacting step, wherein a starting material comprising CBD is contacted with an alkaline zeolite catalyst, thereby forming a reaction mixture; and
   (2) a conversion step, wherein at least about 10% by weight of the CBD in the reaction mixture is converted to THC, thereby forming a product mixture comprising THC.

2. The method of claim 1 wherein the zeolite catalyst comprises one or more natural zeolites selected from the group consisting of analcime, chabazite, clinoptilolite, erionite, mordenite, phillipsite, and ferrierite.

3. The method of claim 1 wherein the zeolite catalyst comprises one or more synthetic zeolites selected from the group consisting of Linde Type A, Linde Type B (zeolite P), Linde Type F, Linde Type L, Linde Type W, Linde Type X, Linde Type Y, Silicalite-1, ZSM-5, SSZ-32, and Zeolite-Beta.

4. The method of claim 1 wherein the alkaline zeolite catalyst is prepared by contacting a zeolite with a weak base.

5. The method of claim 4 wherein the alkaline zeolite catalyst prepared by contacting a zeolite with a weak base comprising sodium bicarbonate for a period of at least about 15 minutes.

6. The method of claim 1 wherein the conversion step comprises stirring the reaction mixture.

7. The method of claim 1 wherein the starting material comprises CBD in an amount of at least about 50% by weight.

8. The method of claim 1 wherein the reaction mixture comprises the zeolite catalyst in an amount of from about 0.1% by weight to about 20% by weight.

9. The method of claim 1 wherein the reaction mixture comprises CBD and the zeolite catalyst in a molar ratio of at least about 1:1.

10. The method of claim 1 wherein the reaction mixture comprises CBD and the zeolite catalyst in a molar ratio of from about 3:1 to about 50:1.

11. The method of claim 1 wherein at least about 70% by weight of the CBD in the starting material is converted to THC in the product mixture.

12. The method of claim 1 wherein the product mixture comprises $\Delta^8$-THC and $\Delta^9$-THC.

13. The method of claim 11 wherein the ratio of $\Delta^9$-THC to $\Delta^8$-THC in the product mixture is greater than 1:1.

14. The method of claim 11 wherein the ratio of $\Delta^9$-THC to $\Delta^8$-THC in the product mixture is at least about 5:1.

15. The method of claim 1 wherein at least about 20% of the total amount of THC in the product mixture is $\Delta^9$-THC.

16. The method of claim 1 wherein at least about 60% of the total amount of THC in the product mixture is $\Delta^9$-THC.

17. The method of claim 1 wherein the conversion step is conducted under
   (a) a vacuum; or
   (b) an atmosphere consisting essentially of nitrogen.

18. The method of claim 1 wherein the conversion of CBD to THC is monitored by (1) collecting one or more samples of the reaction mixture; and (2) analyzing the one or more samples using gas chromatography or high pressure liquid chromatography.

19. The method of claim 1 wherein the reaction mixture further comprises a solvent selected from the group consisting of alcohols, alkanes, edible oils, emulsifiers, and surfactants.

20. The method of claim 1 further comprising a separation step wherein at least a portion of the zeolite catalyst is removed from the product mixture.

21. A method of converting CBD to THC, the method comprising:
   contacting a starting material comprising CBD with a zeolite catalyst, thereby forming a reaction mixture; and
   heating the reaction mixture to a temperature of at least about 120° C. for a period of at least about 30 minutes; thereby forming a product mixture comprising THC.

22. The method of claim 21 wherein the zeolite catalyst is an alkaline zeolite catalyst prepared by contacting a zeolite with a weak base.

23. The method of claim 22, wherein the reaction mixture is heated to a temperature of from about 125° C. to about 175° C.

24. The method of claim 22 wherein the conversion of CBD to THC is halted by cooling the reaction mixture to a temperature of less than about 80° C.

* * * * *